United States Patent [19]
Wurster

[11] Patent Number: 6,066,145
[45] Date of Patent: May 23, 2000

[54] MULTI-LIGATOR DEVICE THAT GENERATES A SIGNAL WHEN A LIGATION RING IS RELEASED

[76] Inventor: Helmut Wurster, Mozartstrasse 20, 75038 Oberderdingen, Germany

[21] Appl. No.: 09/276,967

[22] Filed: Mar. 26, 1999

[30] Foreign Application Priority Data

Mar. 26, 1998 [DE] Germany ............... 298 05446 U
Sep. 5, 1998 [DE] Germany ............... 298 23 317 U

[51] Int. Cl.⁷ .................................................. A61B 17/04
[52] U.S. Cl. ........................... 606/141; 606/140; 606/144
[58] Field of Search ................................ 606/139, 140, 606/141, 144, 148

[56] References Cited

U.S. PATENT DOCUMENTS

| 5,207,690 | 5/1993 | Rohrabacher et al. | 606/135 |
| 5,398,844 | 3/1995 | Zaslavsky et al. | 606/140 |
| 5,462,559 | 10/1995 | Ahmed | 606/140 |
| 5,788,715 | 8/1998 | Watson, Jr. et al. | 606/140 |

*Primary Examiner*—Gary Jackson

[57] ABSTRACT

A multi-ligator device that provides a signal to an operator indicating the release of a ligation ring from the ligator head. Thus, greatly simplifying the use of mechanically decoupled ligator-devices and relieving an operator from having to sense via transmitted vibrations when a ligation ring is detached from a ligator head. The multi-ligator device is constructed using a control unit to operate a ligator head that is connected to the control unit via a flexible shaft. The ligator head supports a plurality of ligation rings that are released by operating the control unit. When a ligation ring is released a signal is generated. The signal can be any one, or a combination, of a mechanical, acoustical, and a visual signal. Additionally, a kit for mounting a ligation ring on a ligator head uses a shaft having a cone-shaped portion to stretch the ligation ring. A lubricant is applied to both the ligation ring and shaft to facilitate the manipulation of the ligation ring. A ring loader is used to push the ligation ring from the tip of the cone shaped portion onto a cylindrical portion of the shaft. Then, a ring pusher is used to push the ligation rings past the cylindrical portion of the shaft and onto the ligator head while the ligator head and the shaft are axially aligned.

20 Claims, 4 Drawing Sheets

MULTI-LIGATOR DEVICE THAT GENERATES A SIGNAL WHEN A LIGATION RING IS RELEASED

BACKGROUND OF THE INVENTION

The present invention relates generally to a multi-ligator device, and associated accessory devices. More specifically, the present invention relates to a multi-ligator device that generates a signal when a ligation ring is released and to an ergonomic accessory kit for mounting the ligation rings onto the ligation head of the present invention.

The ligation of vessels is a commonly used medical procedure. It has long been common to treat lesions, such as hemorrhoids and esophageal varices by ligation. The object of ligation is to position an elastic cord, or ligation ring, around the lesion to stop circulation through the tissue and cause the tissue to die whereupon the body sloughs off the dead tissue. One instrument for facilitating the placement of a single ligating band or a set of bands is a ligator head that can be constructed using two rigid, concentric tubes. The inner tube slides with respect to the outer tube under the manipulation of a control unit that is located at the proximal end of the instrument. A flexible or rigid endoscope having internal passages forming a suction path and a light path interconnect the control unit and the ligator head. The ligator head can be loaded with a set of one or more elastic rings or ligating rings. When the ligator head is located proximate a lesion, a surgeon applies suction to draw tissue into the hollow passage at the distal end of the ligator head. The control unit can then be manipulated to retract the inner tube of the ligator head. This causes the larger diameter of the outer tube to engage the ligating ring and, as the inner tube of the ligator head is withdrawn, a ligation band slides off of the ligator head and elastically contracts around the targeted tissue.

Another type of ligator head that is used has an inner tube that moves axially with respect to an outer tube that is attached to the distal end of an instrument. For example, the outer tube can be attached axially onto the distal end of an endoscope. A control unit then manipulates the ligator head via a rotatable flexible shaft that maintains position on the inner tube so that it does not displace axially outwardly while the instrument is being positioned. Suction can be applied to draw tissue into the central aperture of the ligator head formed by the inner tube. Then, a surgeon manipulates the control unit to retract the inner tube axially past the distal end of the outer tube to force a ligation ring to detach from the ligator head and elastically cinch the targeted tissue.

In German utility model 297 09 170.0 a multi-ligator device for use with endoscopes is described, by which several ligation rings can be placed one after the other at different tissue locations. Advantageously, the inner cylinder of the ligator head onto which the ligation rings are loaded is pulled precisely backwards by a threaded spindle, so that the movement of the endoscope and the compression of the endoscope have no influence on the releasing of the rings.

Despite the advantageous mechanical decoupling contained in German utility model 297 09 170.0, there remains the disadvantage that upon the rotation of the threaded spindle the operator has no direct mechanical feedback corresponding to when a ligation ring is released. This problem did not exist in the older ligator systems that used a mechanically coupled system to control the ligator head. With the older systems, the operator could rely on tactile senses to determine when a ligation ring was released by sensing the vibration transmitted along a cord connecting the ligator head to the control unit.

The present invention overcomes the above drawback that occurs with control units that are mechanically decoupled. This is accomplished by generating a signal that corresponds to the detachment of a ligation ring from the ligator head. Thus, the present invention facilitates the use of a mechanically decoupled ligator device that utilizes more precise movement of the ligator head to increase the accuracy of placement of ligation rings.

SUMMARY OF THE INVENTION

The present invention provides a signal to an operator of a ligation device indicating the detachment of a ligation ring from the ligator head. Thus, facilitating the use of a multi-ligator device by informing the operator when a ligation ring has detached, or "jumped off," the ligator head. The signal can be any one, or combination, of a mechanical, acoustical, and a visual signal.

One embodiment of the present invention uses a signal generator constructed using a piezoelectric sensor mounted on the end of the ligator head to detect the detachment of a ligation ring. The piezoelectric sensor sends an electric signal back to the control unit that is then converted into a signal that will alert the operator that a ligation ring has been released. The electrical signal can be converted into a visual signal causing a light to activate or the electrical signal can be converted to an acoustical signal indicating that a ligation ring has been released.

A second embodiment of the present invention uses the dimensions of the ligation bands to cause the control unit to emit signals at preset conditions that correspond to the release of a ligation ring. This is accomplished by using an indicator disk that is rotatably mounted on the control unit. The position of the indicator disk corresponds to the release of the respective ligation rings. Determining the amount of rotation of the indicator disc that corresponds to the release of a ligation ring is calculated using the thickness of a ligation ring and the proximal displacement of the threaded spindle per rotation of the flexible shaft. The flexible shaft and the threaded spindle rotate together and a mechanical transmission rotates both the flexible shaft and the indicator disc at different rates, the ratio of which can be readily determined.

For example, after releasing a ligation ring, the inner tube of the ligator head can be retracted at least approximately half the width of a ligation ring before the next ligation ring arrives at the edge of the cylinder and is ready to be released. Thus, once the amount of rotation of the threaded spindle that is needed to release a ligation ring is calculated, an indicator disc can have notches positioned along the circumference of the indicator disc. These notches are preferably set at intervals that correspond to the release of individual ligation bands. Additionally, a leaf spring can be mounted in the control unit so as to be biased against the indicator disc. Then, as the indicator disc is rotated the leaf spring clicks into the notches generating an acoustical signal. Thus, by synchronizing the multi-ligator prior to use it is possible to precisely determine, using an acoustical signal, when a ligation band is released.

Additionally, the indicator disc can also have marks placed along the circumference of the indicator disc. These marks are preferably set at intervals that correspond to the release of individual ligation bands. Thus, by synchronizing the multi-ligator prior to use it is possible to precisely determine when a ligation band is released using both an acoustical signal and a dial indicator.

BRIEF DESCRIPTION OF THE DRAWINGS

The foregoing summary, as well as the following detailed description of the invention will be better understood when read in conjunction with appended drawings. For the purpose of illustrating the invention, there are shown in the drawings, embodiments which are presently preferred. It should be understood, however, that the present invention is not limited to the particular arrangements and instrumentalities shown. In the drawings.

DETAILED DESCRIPTION OF THE INVENTION

Figure 1:
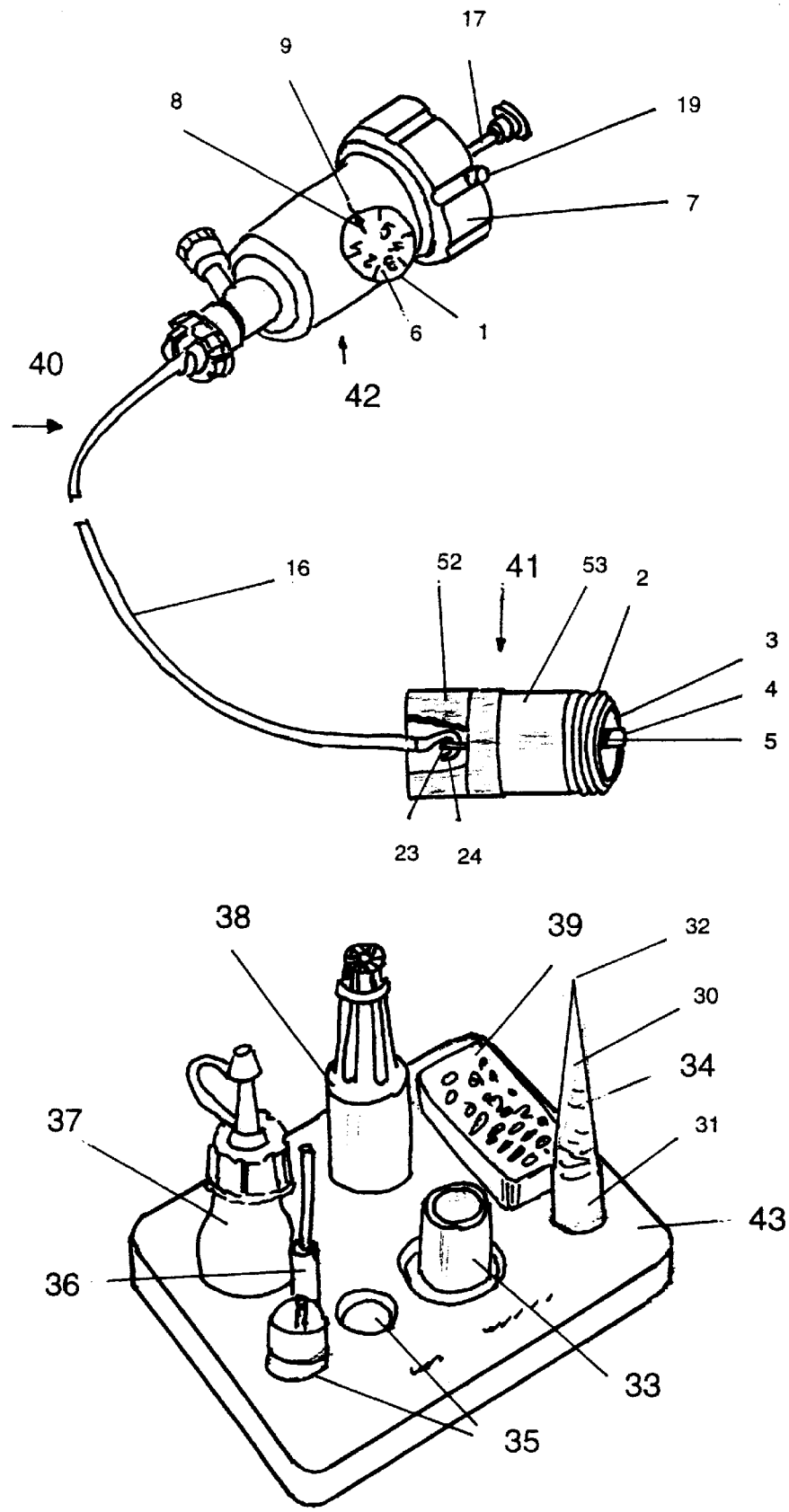
FIG. 1 is a perspective view of a multi-ligation device, and components of an associated kit for mounting the ligation rings on the ligator head of the multi-ligation device, in accordance with the present invention.

Certain terminology is used in the following description for convenience only and is not limiting. The words "right," "left," "lower," and "upper" designate directions in the drawings to which reference is made. The words "inwardly" and "outwardly" refer to directions toward and away from, respectively, the geometric center of the multi-ligator device and designated parts thereof. The terminology includes the words above specifically mentioned, derivatives thereof and words of similar import.

Referring to the drawings in detail, wherein like numerals indicate like elements throughout, there is shown in FIGS. 1–5 a preferred embodiment of a multi-ligator device 40 and the associated kit components 33–39 for mounting the ligation rings 2 onto the ligator head 41. The multi-ligator device 40 is used in conjunction with an endoscope (not shown). The control unit 42 is attached to the proximal end of the endoscope channel and the ligator head 41 is attached to the distal end of the endoscope by a rubber sleeve 52. The rubber sleeve 52 also provides a seal between the endoscope and the ligator head 41 during the suction portion of the medical procedure. The flexible shaft 16 occupies an internal passage of the endoscope and provides the tension necessary to maintain the ligator head 41 in place on the distal end of the endoscope.

Figure 4:
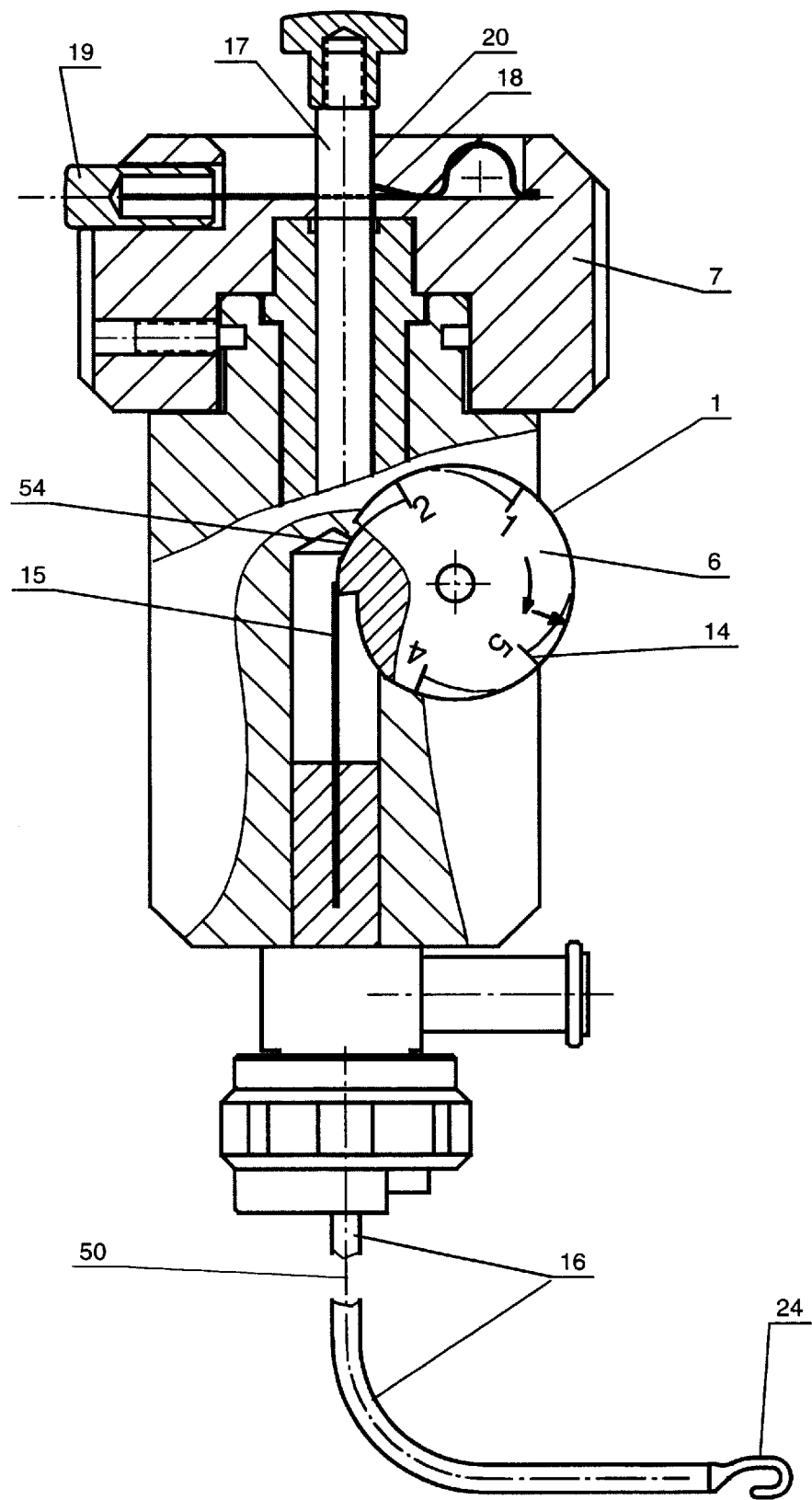
FIG. 4 is a partial cross-sectional view of the control unit of the multi-ligation device according to a second embodiment of the present invention.
Figure 5:
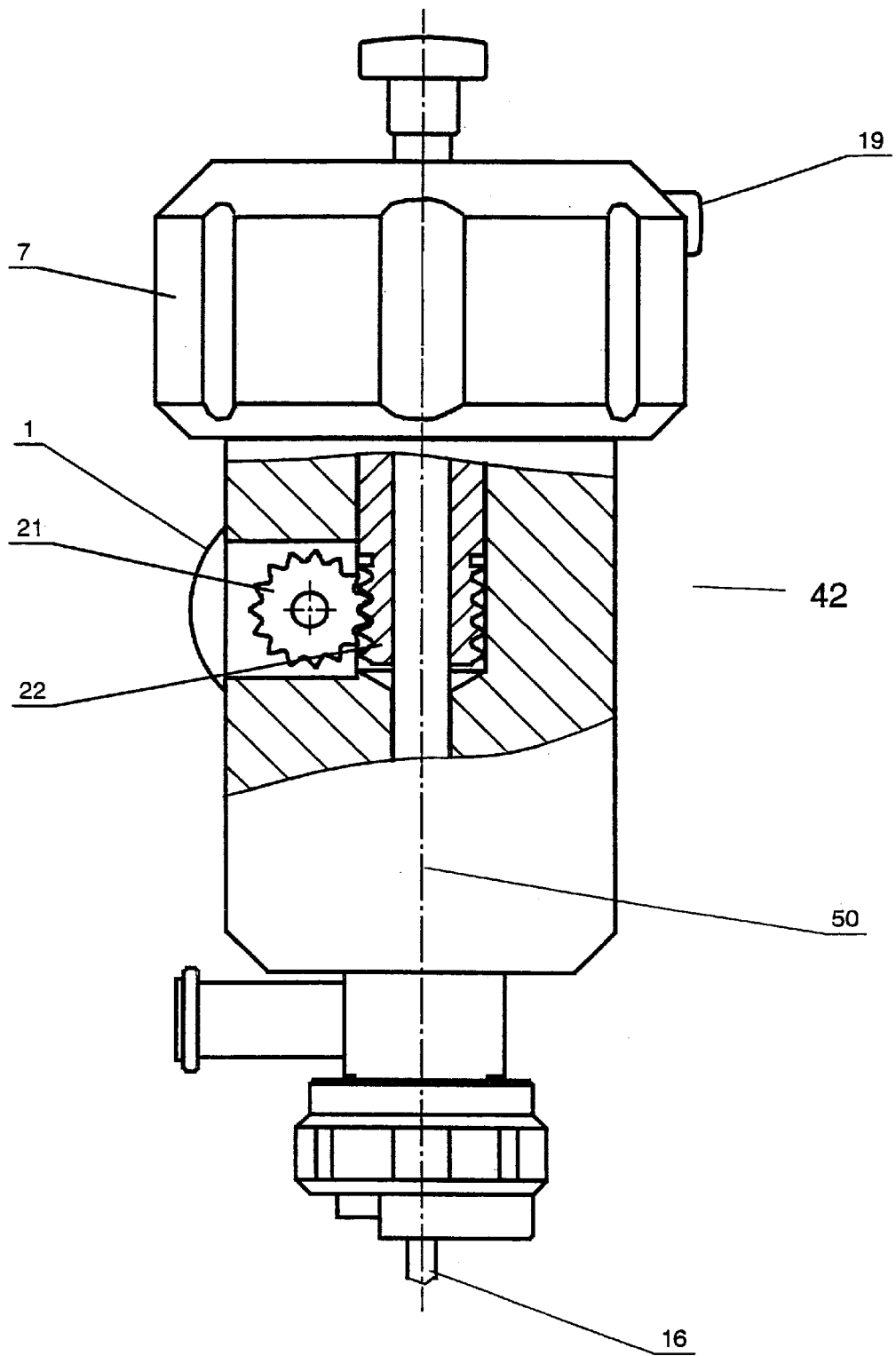
FIG. 5 is a second partial cross-sectional view of the control unit of the multi-ligation device of either FIG. 1 or FIG. 4.

Referring to FIGS. 1, 4, and 5, a control unit 42 is shown that is connected to a ligator head 41 via a flexible shaft 16, that passes through the body of the control unit 42. As shown in FIG. 1, the flexible shaft 16 is attached at one end using a hook 24 to the ligator head 41. The hook 24 engages an eye of the threaded spindle 23 that is mounted to the inner cylinder 3 of the ligator head 41. The flexible shaft 16 and the threaded spindle 23 are rotated by the rotation of the hand wheel 7. As shown in FIG. 4, the portion of the flexible shaft 16 that protrudes past the top of the control unit 42 is referred to as the driving portion 17 of the flexible shaft 16. Movement of the flexible shaft 16 should only be permitted in the proximal direction and should be blocked in the distal direction. The proximal direction is the upward direction and the distal direction is the downward direction, as viewed in FIG. 4. The centerline 50, shown in FIGS. 4 and 5, shows the axial center of the flexible shaft 16.

Movement of the flexible shaft 16 in the distal direction should only be possible after operating an unlocking device. The displacement of the flexible shaft 16 in the distal direction is necessary for properly engaging the hook 24 with the eye of the threaded spindle 23 of the ligator head 41. However, after the multi-ligator device 40 is ready for use, it is preferable to prevent the flexible shaft 16 from moving in the distal direction. This is necessary to prevent the ligator head 41 from detaching from the endoscope (not shown). Locking is achieved by incorporating a spring 18 into the hand wheel 7. The spring 18 presses on the driving portion 17 of the flexible shaft 16. The driving portion is axially moveable into the worm gear 22, when the spring 18 is not engaged with the driving portion 17. The driving portion 17 and the worm gear 22 formed around a portion of the flexible shaft 16 rotate with the hand wheel 7. The driving portion 17 has a knurled side 20 that the spring 18 engages to allow movement in only the proximal direction. While the spring 18 engages the driving portion 17 of the flexible shaft 16, movement in a distal direction is blocked. Thus, only the pulling back of the flexible shaft 16, in the upward (proximal) direction as viewed in FIG. 4, is possible. The spring 18 can be disengaged from the driving portion 17 by laterally pushing the spring 18 using the knob 19, as shown in FIG. 4. Once the spring 18 is disengaged, the driving portion 17 can be moved in the distal direction as long as pressure is maintained on the knob 19. While the preferred embodiment uses a spring 18 to secure the flexible shaft 16 from moving in one direction, it is understood by those of skill in the art from this disclosure that the invention is not limited to any particular method of securing the flexible shaft 16.

As shown in FIG. 5, the control unit 42 uses a mechanical transmission to control the individual release of each ligation ring 2 that is mounted onto the ligator head 41. The mechanical transmission is constructed using a worm gear 22 that is formed around a portion of the flexible shaft 16, as shown in FIGS. 4–5. The hand wheel 7 rotates the worm 22 while it is being rotated by an operator of the multi-ligator device 40. As the hand wheel 7 is rotated, the threaded spindle 23 of the ligator head 41 is rotated by the rotating flexible shaft 16. As the threaded spindle 23 of the ligator head 41 is rotated, a ligation ring 2 is released. This causes the flexible shaft 16 to move slightly in the proximal direction to compensate for the axial distance traveled by the threaded spindle 23 as it rotates through the threads of the ligator head 41.

An indicator disk 1 is attached to the control unit 42. The indicator disk 1 rotates corresponding to the rotation of the flexible shaft 16. As the release of a ligation ring 2 depends on the rotation of the flexible shaft 16, the position of the indicator disk 1 also correlates to the release of the ligation rings 2.

The indicator disk is connected by a worm gear wheel 21 to a worm gear 22 that is mounted around the driving portion 17 of the flexible shaft 16 that is contained inside the control unit 42, as shown in FIG. 5. The worm gear 22 is rotated by the hand wheel 7. The worm gear 22 drives the worm gear wheel 21 that is shown on the left side of the control unit 42 in FIG. 5. Together, both the worm gear wheel 21 and the worm gear 22 cause the indicator disk 1 to rotate in a manner that corresponds to the release of the individual ligation rings 2. The indicator disk 1 is coaxially aligned with and connected to the worm gear wheel 21. The provision of an indicator disc 1, results in a greater precision with regards to determining the timing of the release of ligation rings 2. Accordingly, the indicator disc 1 can provide a visual signal indicating the release of a ligation ring 2.

While in the preferred embodiment the means for controlling the individual release of each ligation ring 2 is using the threaded spindle 23 and the hand wheel 7, it is understood by those of ordinary skill in the art from the disclosure that alternative means for controlling the individual release of each ligation ring 2 from the ligator head 41 can be used. For instance, many other types of mechanical elements can be combined to accomplish the same effect as the threaded spindle 23 and the hand wheel 7.

Cylinders 3, 53 are connected by a threaded spindle 23. Thus, by rotating the threaded spindle 23, the inner cylinder 3 will move in the proximal direction. Accordingly, the release of ligation rings 2 from the ligator head 41 is regulated by the rotation of the flexible shaft 16. As shown in FIG. 1, the ligator head 41 is constructed using two rigid concentric cylinders 3, 53. The inner cylinder 3 is disposed within the outer cylinder 53. The flexible shaft 16 is connected by the hook 24 and the eye of the threaded spindle 23. The inner cylinder 3 is axially displaceable with respect to the outer cylinder 53 under the manipulation of the control unit 42. The multi-ligator device can be used with a flexible or rigid endoscope (not shown) having internal passages forming a suction path and a channel to interconnect the control unit 42 and the ligator head 41. The flexible shaft 16 would be contained in a channel inside the endoscope. Thus, by manipulation of the hand wheel 7, the flexible shaft 16 is rotated. This causes the threaded spindle 23 to rotate and to pull the inner cylinder 3 inside of the outer cylinder 53. This causes the release of one of the ligation rings 2.

While the preferred embodiment uses a concentric cylinder design for the ligator head 41, those of ordinary skill in the art will understand from this disclosure that this invention is not limited to any particular type of ligator head 41. Additionally, more complicated and advanced ligator heads could also be used with a signal generator that indicates the release of a ligation ring 2 from the ligator head 41.

The preferred embodiment of the multi-ligator device has a signal generator that generates a signal when one of the ligation rings 2 is released from the ligator head 41. As shown in FIG. 1, a first embodiment of the present invention has a signal generator that is constructed using a piezoelectric element 5 that is disposed on an elastic member 4 to generate an electric signal when one of the ligation rings 2 is detached from the ligator head 41. The elastic member 4 is preferably a spring that will be touched by the ligation ring 2 when the ligation ring 2 is released from the ligator head 41. Once the spring 4 is touched by the ligation ring 2, the spring 4 will vibrate and the piezoelectric element 5 will transform the mechanical energy into an electric signal. This signal generator must be built very small and should not have any sharp edges that could either create injuries during the use of the multi-ligator device 40 or interfere with the proper use of the multi-ligator device 40. The electric signal is transmitted via cables (not shown) that must also be placed in the endoscope channel together with the flexible shaft 16. The electrical signal could be used by the monitor (not shown) that displays the endoscopic image, or the signal could be transformed into either one of an acoustical signal and a light signal that is separately displayed from the monitor. The light signal can be displayed on the control unit 42. Alternatively, the light signal can be displayed in an area more convenient for the operator of the multi-ligator device 40 to view while operating the multi-ligator device 40. In addition, the electrical signal can be transformed into an acoustical signal that alerts the operator of the multi-ligator device that a ligation ring 2 has been released from the ligator head 41.

A multi-ligator device 40 that uses a piezoelectric element 5 as part of a signal generator has the advantage of directly indicating the release of a ligation ring 2. However, the use of a piezoelectric element 5 requires that the multi-ligator device 40 be carefully designed to facilitate the proper handling and sterilization of the device. The cables (not shown) for the transmission of the electrical signal must be placed in the endoscope channel (not shown) together with the flexible shaft 16, which restricts the space in the endoscope channel. Also, the ligator head 41 must be connected to these cables using a miniaturized, electrical plug connector (not shown).

A second embodiment of the multi-ligator device, shown more exactly in FIG. 4, illustrates a multi-ligator device 40 that uses a signal generator that uses only mechanical elements to generate a signal indicating the release of a ligation ring 2 from the ligator head 41. This is accomplished by placing a plurality (e.g. five) of notches 14 around the circumference of the indicator disk 1. The notches 14 do not have to be on the outer face of the indicator disk 1, as shown in FIG. 4, but can be on the side of the indicator disk 1 that is in contact with the control unit 42. A leaf spring 15 is mounted inside the control unit 42 and biased against the indicator disk 1. As shown in FIG. 4, the leaf spring slides along a crest 54 between the notches 14 until reaching the next notch 14. After passing a predetermined position, the leaf spring 15 snaps into a notch 14 generating an acoustical signal. This acoustical signal can be modified by varying the material used to construct the leaf spring 15 and the material used inside of the notches 14. The acoustical signal can be further optimized by adding some stiffening corrugations to the leaf spring 15. In addition, the notches 14 can be located around the circumference of the indicator disk 1 to correspond to the release of respective ligation rings 2 from the ligator head 41.

Calculating the position of the notches 14 is done using the known width of the ligation ring 2 and the amount of rotation of the indicator disk per an amount of rotation of the flexible shaft 16. The worm gear 22, the flexible shaft 16, and the threaded spindle 23 undergo substantially identical rotation. For a given amount of rotation of the threaded spindle 23, hand wheel 7, the worm gear 22, and the flexible shaft 16, the inner cylinder 3 is rotated causing the inner cylinder 3 to retract into the outer cylinder 53, as shown in FIG. 1. During the time that the threaded spindle 23 is being rotated, the worm gear 22 is also rotating the indicator disc 1 via the worm gear wheel 21. Thus, by knowing the amount of rotation of the indicator disc 1 that occurs for a given amount of displacement of the cylinder 3 by threaded spindle 23, a ratio can be determined for how much rotation of the indicator disc 1 will occur when the cylinder 3 is displaced a predetermined amount. Since the width of a ligation ring 2 is known, the above-described ratio can be used to determine the amount of rotation of the indicator disc 1 that will occur before each ligation ring 2 is released from the ligator head 41.

Additionally, as shown FIGS. 1 and 4, a plurality of markings 6 can be placed on the outer surface of the indicator disk 1 to correspond with the release of respective ligation rings 2. Depending on the design of the mechanical elements used by the control unit 42 to rotate the flexible shaft 16, it is possible to attain a desired level of precision in the release of a ligation ring 2 from the ligator head 41. At the beginning of the operation, the hand wheel 7 is used to manipulate the position of the indicator disk 1 so that the start arrow 8 located on the indicator disc 1 is oriented opposite to the mark 9 which is located on the control unit 42. This alignment procedure forces the markings 6, 8 on the indicator disk 1 to properly correspond to the releasing of the ligation rings 2. As the operator will not always be able to easily view the indicator disc 1, it is advantageous if the markings 6,8 are placed both on the circular outer surface of the indicator disc 1, as well as on the peripheral circumferential surface of the indicator disc 1.

The mechanical elements used by the control unit 42 can be designed so that the indicator disk 1 undergoes a full rotation before a ligation ring 2 is released. Alternatively, the control unit 42 can be designed so that multiple ligation rings 2 can be released while the indicator disc 1 undergoes only one rotation. In some situations, an optical indicator alone is not always useful, since during the use of the multi-ligator device 40 an operator cannot always concentrate on the indicator disc 1. Accordingly, the preferred embodiment also generates an acoustical signal that is easier for an operator to notice without being distracted from performing the medical procedure.

Figure 2:
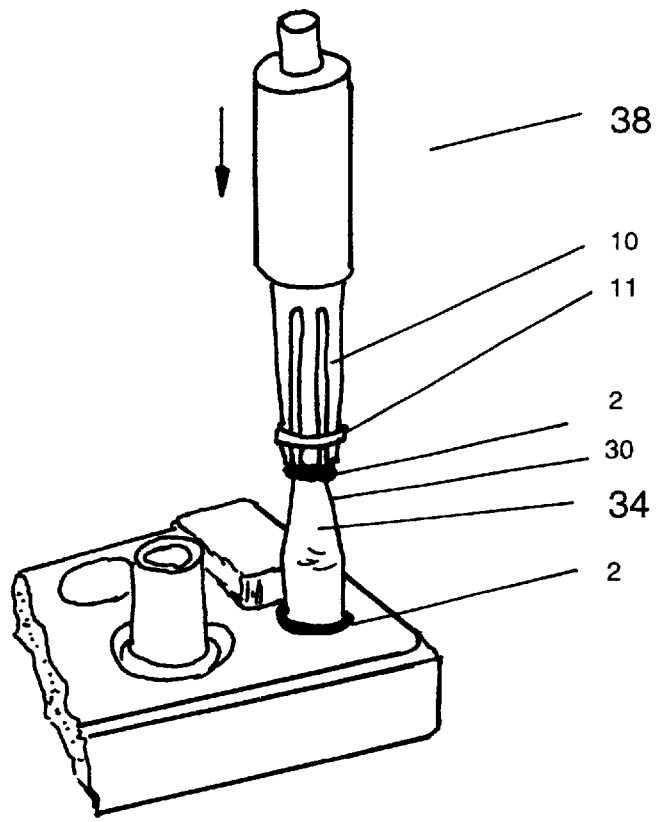
FIG. 2 is a side elevational view of some of the kit components of FIG. 1 illustrating the preparation of ligation rings for mounting on the multi-ligation device of FIG. 1.
Figure 3:
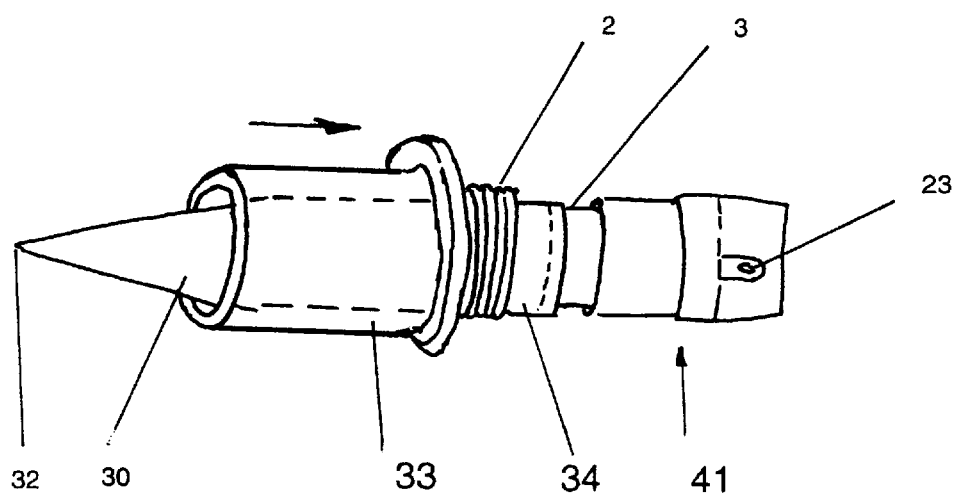
FIG. 3 is an enlarged side elevational view illustrating the use of some of the kit components of FIG. 1 to mount ligation rings on the multi-ligation device of FIG. 1.

A kit for mounting ligation rings 2 on a ligator head 41 is shown in the lower portion of FIG. 1. A shaft 34 having a cone-shaped portion 30 is used to stretch the ligation rings 2. A lubricant 37 is placed on the cylinder 3 and the shaft 34. A ring loader 38 is used to push a ligation ring 2, that is positioned over the tip 32 of the cone-shaped portion 30 of the shaft 34, from the tip 32 past the cone-shaped portion 30 onto the cylindrical portion 31. As also shown in FIG. 2, the ring loader 38 has a plurality of bendable arms 10 that are joined at one end by a circular spring 11. As shown in FIG. 3, a ring pusher 33 is used to push all the ligation rings 2 past the cylindrical portion 31 of the shaft 34 and onto the cylinder 3 of the ligator head 41 while the cylinder 3 of the ligator head 41 and the shaft 34 are axially aligned. A box 39 contains a plurality of ligation rings that are used with the kit shown in FIG. 1. In addition a pallet, or tray, 43 has a plurality of ergonomically shaped and positioned recesses to facilitate the use of the various components of the kit while mounting ligation rings 2 on a ligator head 41.

As shown in FIG. 2, the ligation ring 2 is placed on the shaft 34 and then covered by the ring loader 38. Then, the ring loader 38 is pressed downwards forcing the ligation ring 2 to expand as it travels downward over the cone-shaped portion 30 of the shaft 34. Once a ligation ring 2 passes the cone-shaped portion 30 of the shaft 34, the ligation ring 2 has been stretched to an appropriate size for mounting onto the ligator head 41. When all the ligation rings 2 have been properly stretched and are past the cone-shaped portion 30 of the shaft 34, as shown in FIG. 3, the inner cylinder 3 of the ligator head 41 and the shaft 34 are axially aligned. Before transferring the ligation rings to the ligator head 41, the cylinder 3 must be extended distally from the outer cylinder 53 by rotating the threaded spindle 23 using the extender 36. After axially aligning the ligator head 41 and the shaft 34, the ring pusher 33 is used to push the ligation ring 2 from the shaft 34 onto the cylinder 3 of the ligator head 41. Thus, this kit allows for a simplified method of loading ligation rings 2 onto a ligator head 41.

As shown in FIGS. 1, 4, and 5, the multi-ligator device is used in operation as follows. An operator positions the ligator head 41 proximate a tissue lesion (not shown). Then, by rotating the hand wheel 7, the flexible shaft 16 is rotated. This causes the threaded spindle 23 to move in the proximal direction and pull the inner cylinder 3 inside of the outer cylinder 53 of the ligator head 41 to release one of the ligation rings 2.

In a first embodiment, the release of a ligation ring 2 is detected by a piezoelectric element 5 that is disposed on an elastic member 4 that is attached to the ligator head 41. The electrical signal generated by the piezoelectric element 5 is transferred via cables (not shown) to the control unit 42 and is then transformed into either of an acoustical signal and a visual signal. Alternatively, both an acoustical and a visual signal can be generated in response to the electrical signal from the piezoelectrical element 5. This signal alerts the operator that a ligation ring 2 has been released from the ligator head 41.

A second embodiment of the multi-ligator device generates a mechanical signal indicating the release of a ligation ring 2 from the ligator head 41. As the indicator disk 1 is rotated, a leaf spring 15 snaps into one of a plurality of notches 14 that are positioned around a circumference of the indicator disk 1. The position of the notches correspond to the release of the ligation ring 2 from the ligator head 41. The acoustical signal generated by the impact between the leaf spring 15 and the notch 14 alerts the operator of the multi-ligator device that a ligation ring 2 has been released from the ligator head 41.

From the foregoing description, it can be seen that the present invention comprises a multi-ligator device that generates a signal indicating the release of a ligation ring from the ligator head. It will be appreciated by those skilled in the art that many changes and modifications may be made to the above-described embodiment without departing from the inventive concept thereof. It is understood, therefore, that the present invention is not limited to the particular embodiment of the multi-ligator device disclosed, but it is intended to include all modifications and changes which are within the scope and spirit of the invention as defined by the appended claims.

I claim:

1. A multi-ligator device that generates a signal when a ligation ring is released, comprising:
    a control unit that regulates the individual release of each of a plurality of ligation rings;
    a ligator head releaseably supporting the plurality of ligation rings;
    a flexible shaft connecting the control unit to the ligator head; and
    a signal generator that generates the signal when one of the plurality of ligation rings is released from the ligator head.

2. The multi-ligator device of claim 1, further comprising a spring attached to the control unit and abutting the flexible shaft to hinder the flexible shaft moving in a manner that would increase a length of the flexible shaft between the control unit and the ligator head.

3. The multi-ligator device of claim 1, wherein the signal generator comprises an indicator disc rotatably mounted on the control unit, the indicator disk rotating in correspondence to the rotation of the flexible shaft, a position of the indicator disc providing an optical signal corresponding to the release of each of the plurality of ligation rings.

4. The multi-ligator device of claim 1, wherein the signal generator comprises a piezoelectric element disposed on an elastic member mounted on the ligator head, the piezoelectric element generating the signal when one of the plurality of ligation rings is released from the ligator head.

5. The multi-ligator device of claim 4, wherein the signal from the piezoelectric element is transformed into either one of an acoustical signal and a light signal.

6. The multi-ligator device of claim 5, further comprising:
    a hand wheel rotatably attached to the control unit and controlling the rotation of the flexible shaft; and the hand wheel being rotatable to cause a threaded spindle to rotate and thereby cause the ligator head to release one of the plurality of ligator rings.

7. The multi-ligator device of claim 6, further comprising:

an indicator disc rotatably mounted on the control unit, the indicator disk rotating in correspondence to the rotation of the flexible shaft;

a worm gear attached to the hand wheel;

a worm gear wheel engaged with the worm gear and engaged with the indicator disc; and the worm gear rotating with the hand wheel and driving the worm gear wheel thereby rotating the indicator disc.

8. The multi-ligator device of claim 7, further comprising:

the indicator disc bearing a plurality of notches; and a leaf spring mounted in the control unit and biased against the indicator disc, the leaf spring generating the acoustical signal when the indicator disc is rotated to cause the leaf spring to snap into one of the plurality of notches.

9. The multi-ligator device of claim 8, wherein each of the plurality of notches is positioned to correspond to the release of one of the plurality of ligation rings.

10. The multi-ligator device of claim 9, further comprising a plurality of markings on the indicator disc, each of the plurality of markings positioned to correspond to the release of one of the plurality of ligation rings.

11. The multi-ligator device of claim 1, wherein the signal generator comprises:

an indicator disc rotatably mounted on the control unit, the indicator disk rotating in correspondence to the rotation of the flexible shaft; and a leaf spring mounted in the control unit and biased against the indicator disc, the leaf spring generating an acoustical signal when the indicator disc is rotated to cause the leaf spring to snap into one of the plurality of notches.

12. The multi-ligator device of claim 11, further comprising:

an elastic member mounted on the ligator head;

a piezoelectric element disposed on the elastic member and generating a second signal when one of the plurality of ligation rings is released from the ligator head.

13. The multi-ligator device of claim 11, wherein each of the plurality of notches is positioned to correspond to the release of one of the plurality of ligation rings.

14. The multi-ligator device of claim 13, further comprising:

a hand wheel rotatably attached to the control unit and engaged with the flexible shaft; and the hand wheel being rotatable to cause a threaded spindle to rotate and thereby cause the ligator head to release one of the plurality of ligator rings.

15. The multi-ligator device of claim 14, further comprising:

a worm gear attached to the hand wheel;

a worm gear wheel engaged with the worm gear and engaged with the indicator disc; and the worm gear rotating with the hand wheel and driving the worm gear wheel thereby rotating the indicator disc.

16. The multi-ligator device of claim 15, further comprising a plurality of markings on the indicator disc, each of the plurality of markings positioned to correspond to the release of one of the plurality of ligation rings.

17. A kit for mounting of a ligation ring on a ligator head, comprising:

a shaft having a cone-shaped portion for stretching the ligation ring;

a lubricant for lubricating an inner cylinder of the ligation head and the shaft;

a ring loader for pushing the ligation ring, that is positioned over a tip of the cone-shaped portion of the shaft, from the tip past the cone-shaped portion;

an extender for moving the inner cylinder outward from the ligator head; and a ring pusher for pushing a plurality of ligation rings past the cylindrical portion of the shaft and onto the ligator head while the ligator head and the shaft are axially aligned.

18. The kit of claim 17, wherein the ring loader has a plurality of bendable arms joined at one end by a circular spring.

19. The kit of claim 18, further comprising a box containing a plurality of ligation rings.

20. The kit of claim 19, further comprising a pallet having a plurality of shaped recesses for accommodating the box, the shaft, a bottle of the lubricant, the ring loader, the extender, the ring pusher, and two ligator heads therein.

* * * * *